(12) United States Patent
Bridenbaker

(10) Patent No.: US 8,951,802 B2
(45) Date of Patent: Feb. 10, 2015

(54) CORROSION TESTING USING AN AUTOMATED OSCILLATING SOLUTION SPRAY MANIFOLD

(71) Applicant: The Singleton Corporation, Cleveland, OH (US)

(72) Inventor: Eric Bridenbaker, Avon Lake, OH (US)

(73) Assignee: The Singleton Corporation, Cleveland, OH (US)

( * ) Notice: Subject to any disclaimer, the term of this patent is extended or adjusted under 35 U.S.C. 154(b) by 210 days.

(21) Appl. No.: 13/622,518

(22) Filed: Sep. 19, 2012

(65) Prior Publication Data

US 2013/0109099 A1  May 2, 2013

Related U.S. Application Data

(60) Provisional application No. 61/536,328, filed on Sep. 19, 2011.

(51) Int. Cl.
*G01N 17/00* (2006.01)

(52) U.S. Cl.
CPC .................................. *G01N 17/002* (2013.01)
USPC ................................................. 436/6; 422/53

(58) Field of Classification Search
USPC ................................................. 422/53; 436/6
See application file for complete search history.

(56) References Cited

U.S. PATENT DOCUMENTS

| | | | | |
|---|---|---|---|---|
| 2,523,322 A | * | 9/1950 | Ornstein et al. ................ | 374/57 |
| 2,897,060 A | * | 7/1959 | Dieman .......................... | 422/53 |
| 3,131,029 A | * | 4/1964 | Dieman .......................... | 422/53 |
| 3,163,497 A | * | 12/1964 | Gill ................................. | 422/53 |
| RE25,932 E | * | 12/1965 | Neffenger ...................... | 422/53 |
| 3,273,802 A | * | 9/1966 | Hull, Jr. ......................... | 239/338 |
| 3,542,517 A | * | 11/1970 | Gill ................................. | 422/53 |
| 3,650,281 A | * | 3/1972 | Hurst ............................. | 134/58 R |
| 3,886,791 A | * | 6/1975 | Grossman ..................... | 73/150 R |
| 4,069,019 A | * | 1/1978 | Suga .............................. | 422/53 |
| 4,092,122 A | * | 5/1978 | Suga .............................. | 422/53 |
| 4,689,472 A | * | 8/1987 | Singleton et al. ............. | 392/405 |
| 4,741,351 A | * | 5/1988 | Minkin .......................... | 134/144 |

(Continued)

OTHER PUBLICATIONS

HCL (Hawaii Corrosion Lab) facilities web page Copyright 2009 showing Accelerated Corrosion Testing Equipment downloaded Jun. 11, 2014 from http://hawaiicorrosionlab.org/facilities/facilities_acorrosion.htm.*

*Primary Examiner* — Arlen Soderquist
(74) *Attorney, Agent, or Firm* — Fay Sharpe LLP

(57) ABSTRACT

A method of testing workpieces and an automated oscillating solution spray manifold assembly for a corrosion testing chamber is configured to introduce a fluid into a cavity of a test cabinet that receives workpieces. The manifold assembly includes a motor having an output shaft for driving a linkage assembly. An elongated spray bar is connected to the linkage assembly and the spray bar has a plurality of openings spaced therealong. The linkage assembly is configured to rotate the spray bar in a desired oscillatory movement such that fluid can be dispensed through the openings and into the test cabinet. A fan-like pattern sprays from one opening and substantially overlaps with spray from at least one adjacent opening. The method of testing may include one or more of the steps of controlling a speed of the motor, a temperature level of the cavity, a humidity level of the cavity, and a salinity content of the fluid within the cavity of the test cabinet.

19 Claims, 5 Drawing Sheets

(56) References Cited

U.S. PATENT DOCUMENTS

| | | | |
|---|---|---|---|
| 4,752,446 A * | 6/1988 | Singleton et al. | 422/53 |
| 4,779,468 A * | 10/1988 | Susuki | 73/865.6 |
| 4,995,273 A * | 2/1991 | Kisima et al. | 73/865.6 |
| 5,228,949 A * | 7/1993 | Ketelhohn et al. | 216/92 |
| 5,476,636 A * | 12/1995 | Tomiita et al. | 422/53 |
| 5,782,252 A * | 7/1998 | Lewis et al. | 134/103.1 |
| 5,824,918 A | 10/1998 | Zuk | |
| 6,533,452 B1 * | 3/2003 | Hardcastle, III | 374/57 |

\* cited by examiner

CORROSION TESTING USING AN AUTOMATED OSCILLATING SOLUTION SPRAY MANIFOLD

This application claims the priority benefit of U.S. provisional application Ser. No. 61/536,328, filed 19 Sep. 2011, the disclosure of which is expressly incorporated herein by reference.

BACKGROUND

This disclosure is directed to an accelerated atmospheric corrosion testing chamber that is used to analyze the impact of temperature, salt, humidity, and other climate parameters on a sample test or work specimens. Selected aspects may find application in related testing environments and applications.

A wide variety of industries test specimens or workpieces are exposed to accelerated corrosion conditions, for example, in a controlled test chamber. One common test relates to introducing a solution such as water or a saline solution into the test chamber to represent a salt load in a natural environment condition, e.g., the application of salt to a roadway to treat snow and ice conditions during winter weather. Test specimens are loaded or mounted within the chamber and a fog, for example, is introduced into the interior cavity of the test chamber housing. A predetermined or variable temperature can be maintained in the housing, along with a predetermined or variable relative humidity, and/or a predetermined or variable salinity content as may be desired for testing the specimens in accordance with government, engineering, and/or customer specifications or standards.

A controller is operatively connected to a heater, fluid or saline source, one or more temperature and humidity sensors disposed in the cabinet chamber, fans, motors, etc. in order to control and obtain feedback regarding the internal environment of the test chamber. The conditions in the chamber are closely controlled, and the data is collected and either stored in a memory associated test chamber, or conveyed to a remote location.

Known corrosion testing chambers often employ a fixed, elongated tube extending across the chamber. Multiple nozzles are spaced at axial locations along the tube for directing the saline solution toward a lower portion of the cabinet. The test specimens—typically mounted in a lower portion of the chamber—are thus exposed to the solution spray directed from overhead. The nozzles may be replaced or substituted if the nozzles become clogged, or in order to provide a different spray pattern.

A need exists for a more complicated application of the solution spray while still protecting the integrity of the testing cabinet components, as well as being able to easily alter the spray pattern without undue manipulation or expense.

SUMMARY

An improved spray mechanism is provided for a test chamber.

In one preferred embodiment, the spray mechanism includes an elongated tube selectively rotated to dispense a spray through a generally arcuate path in the test chamber.

A motor and associated drive components of the spray mechanism are positioned externally of the cabinet to limit any potential exposure to the chamber interior.

The motor speed may be a single speed or varied as desired, and likewise the oscillation angle may be selectively varied by changing a drive link mechanism extending between the motor and the rotating tube.

One advantage of the present disclosure is to provide an oscillating spray to the chamber interior.

Another advantage relates to driving the movable tube from a location external to the test chamber.

Yet another benefit resides in a more uniform spray coverage being applied to the test specimens.

Still other benefits and advantages of the present disclosure will become more apparent upon reading and understanding the following detailed description.

DETAILED DESCRIPTION

Figure 1:
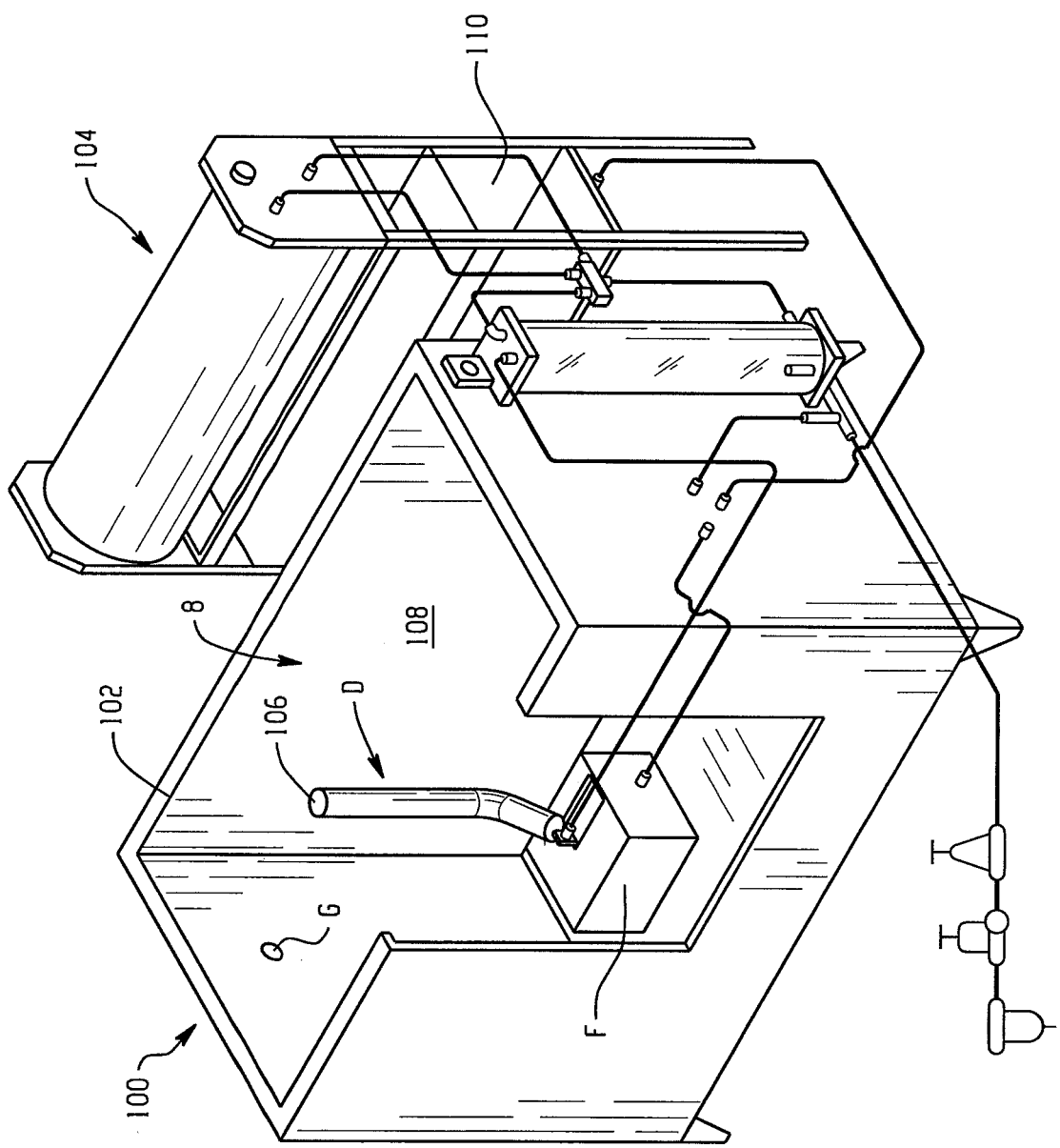
FIG. 1 is a perspective view of a test cabinet with the lid or cover removed.

With reference to FIG. 1, an exemplary corrosion test cabinet 100 is shown. The test cabinet 100 is dimensioned to receive test specimens or workpieces (not shown) that are typically loaded through an opening such as opening 102 provided in an upper portion of the test cabinet. The test cabinet is shown as having a generally rectilinear conformation in cross-section, although other shapes could also be used without departing from the scope and intent of the present disclosure. A first reservoir 104 stores and provides a supply of fluid such as water to create a desired relative humidity or fog as generated by fog generator 106 into a test chamber or cabinet interior 108. Further, a second reservoir referred to here as a salt solution reservoir 110 may provide a desired supply of a saline solution (other than just water) for introduction into the chamber. Of course, one skilled in the art will recognize that other solutions (with or without salt) could be introduced into the chamber than the noted saline solution, for example, plain tap water could be introduced as a solution into the chamber, and that a main and/or secondary solution may be used without departing from the scope and intent of the present disclosure.

Figure 2:
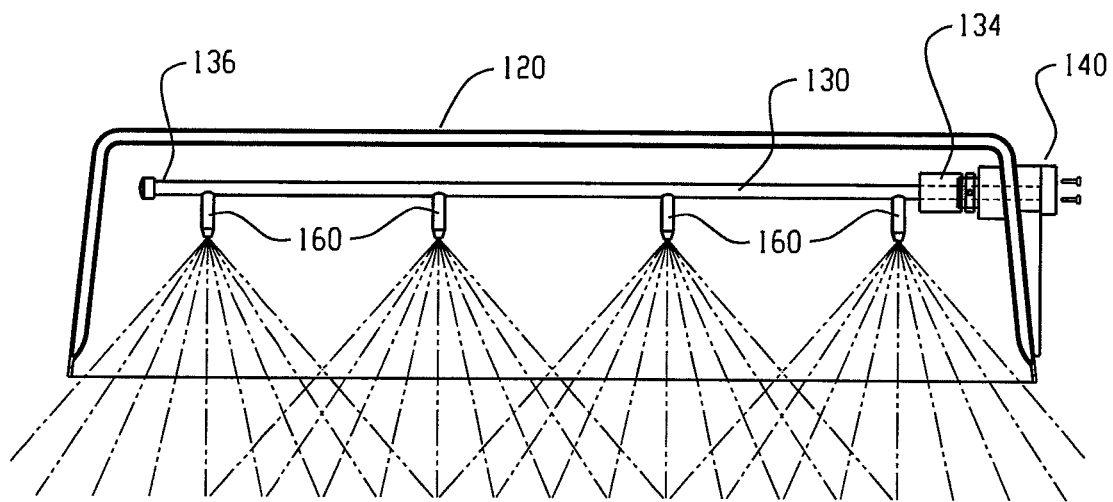
FIG. 2 is an elevational view, partly in cross-section, of a test cabinet lid showing the placement of the oscillating spray manifold or spray bar of the present disclosure.

Lid 120 (FIGS. 2 and 3) is typically hingedly connected to the cabinet along one edge of the cabinet adjacent the opening 102 to selectively open and close the opening to the test chamber 108. It is common to employ a power assist mechanism to facilitate opening and closing of the lid 120 relative to the chamber and assure that the lid seals over the opening during the test procedure, and also to hold the lid open and thereby load and unload the test specimens into the test chamber.

In the particular test cabinet shown in FIG. 1, the solution from reservoir 110 is introduced by way of a spray manifold or spray bar 130 (FIG. 2) into the test chamber 108. The spray bar 130 is preferably mounted in the lid 120 and as perhaps best illustrated in FIGS. 2 and 3, the spray bar is positioned as close to an apex 122 of the lid so that the resultant spray is advantageously situated as high as possible within the cabinet when the lid is closed. The spray bar 130 extends over substantially an entire length of the lid 120. A first end 132 of the spray bar is received in a mounting member or a union 134 that connects the spray bar with a drive assembly 140. A second end 136 is preferably received in a bearing member 138 that provides rotational support for the terminal end 136 of the spray bar.

Figure 3:
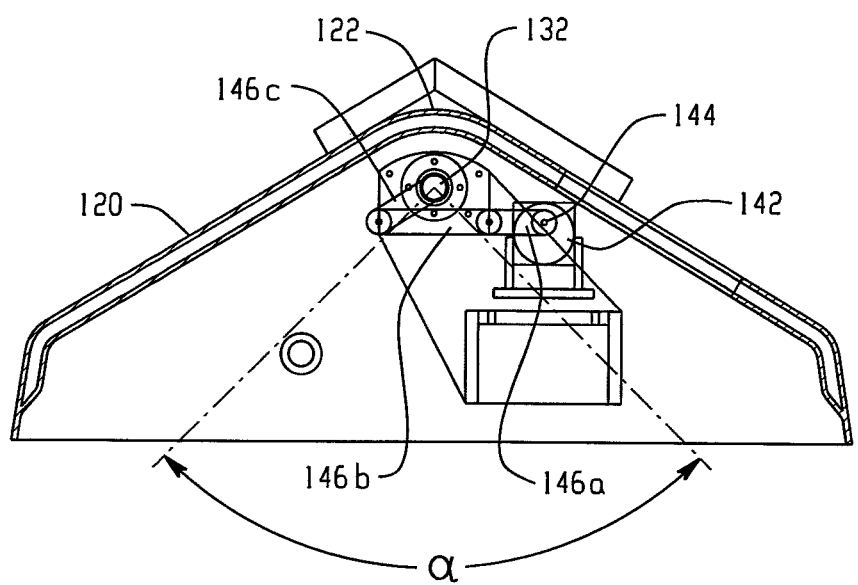
FIG. 3 is an end view, partly in cross-section, of the test cabinet lid of FIG. 2.

The drive assembly includes a motor 142 having an output shaft 144 that drives a linkage assembly 146 connected to the end 132 of the spray bar. As shown, the linkage assembly 146 includes three separate links 146a, 146b, 146c. As the first link 146a is rotated by the driveshaft 144, the first link imparts similar motion through intermediate link 146b to the third link 146c. This rotational motion of the driveshaft and links results in a desired oscillatory movement of the spray bar through a predetermined angle α. Angle α as shown in FIG. 3 is approximately 90°, although selective removal, addition, or substitution of one or more of the links 146a-callows this oscillation angle to be easily altered. Further, the speed of oscillation may be set to a single speed or varied through a range of desired speeds by manual or automatic operator selection via a controller 150 (FIG. 4).

Nozzles 160 are mounted to axially spaced openings (not shown) in the spray bar 130. Preferably, all of the openings, and thus all of the nozzles 160 are disposed along the same circumferential portion of the spray bar (i.e., aligned), although such an arrangement can be modified if so desired. The nozzles 160 are intended to impart a fan-like, preferably substantially uniform spray pattern that impinges on the test specimens situated below the spray bar in the test chamber. The pattern is designed so that the spray from one nozzle substantially overlaps with the spray from at least one adjacent nozzle.

Figure 4:
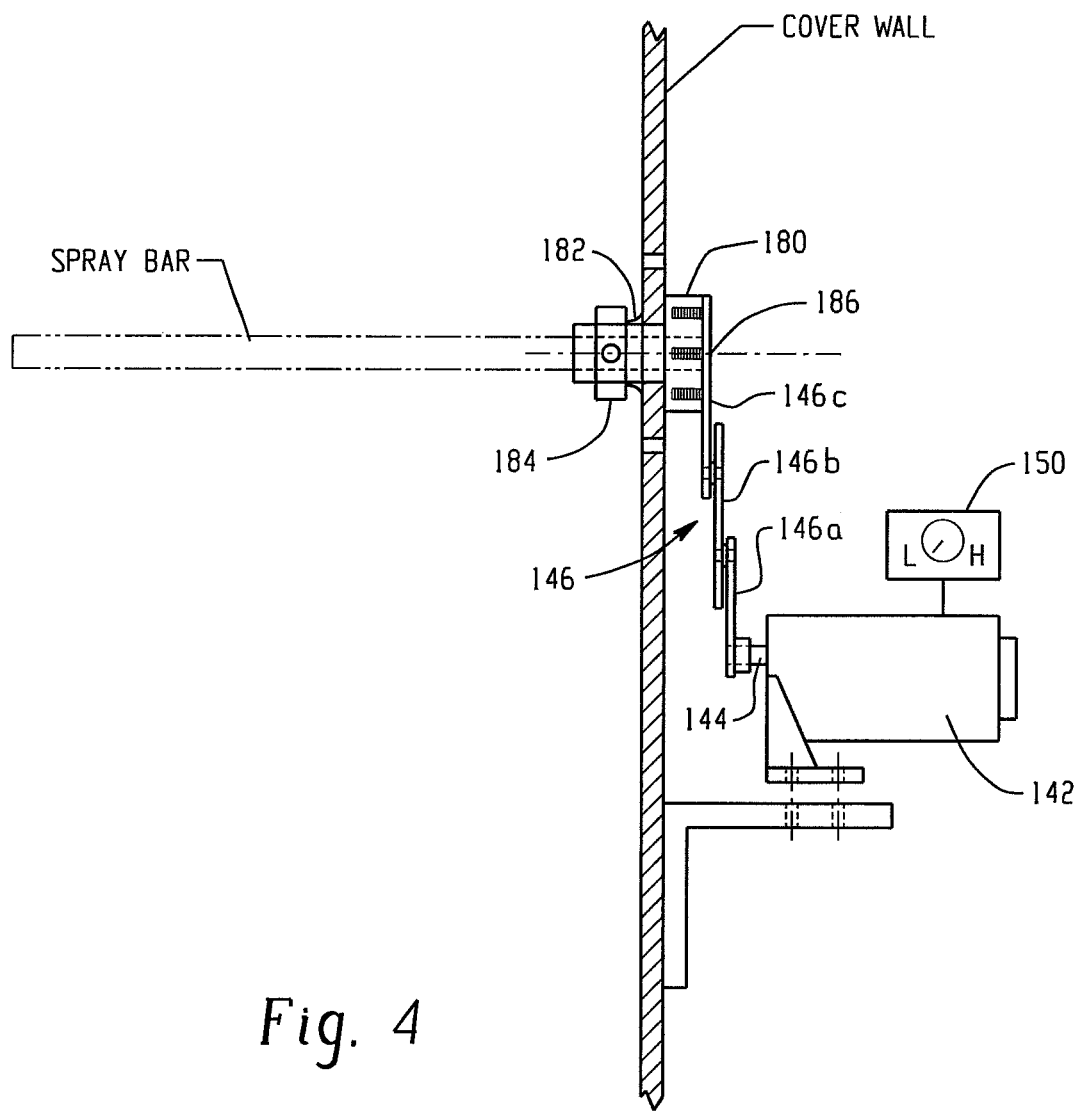
FIG. 4 is an enlarged elevational view of the drive assembly for the spray bar.
Figure 5:
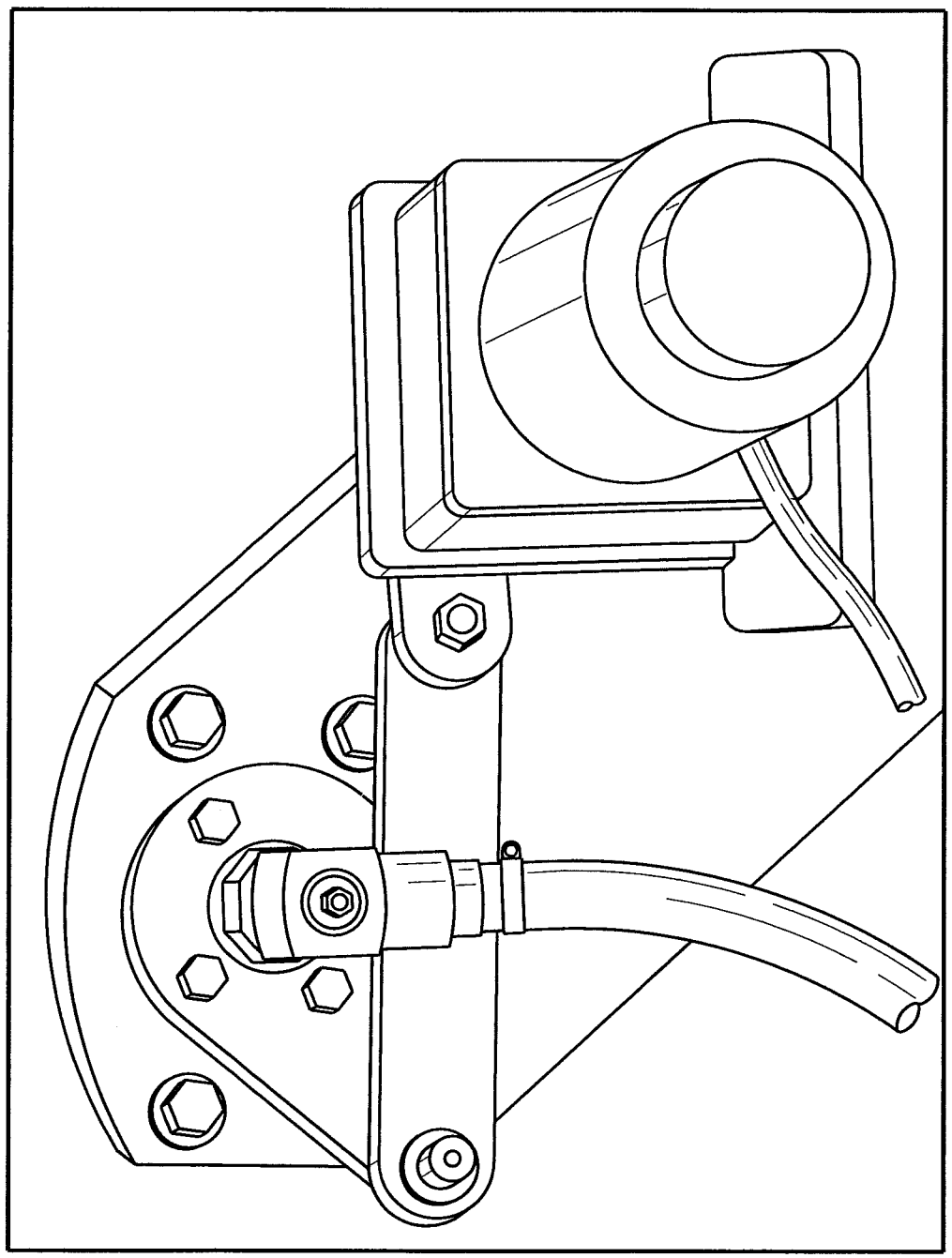
FIG. 5 is an enlarged image of the drive assembly for the spray bar.
Figure 6:
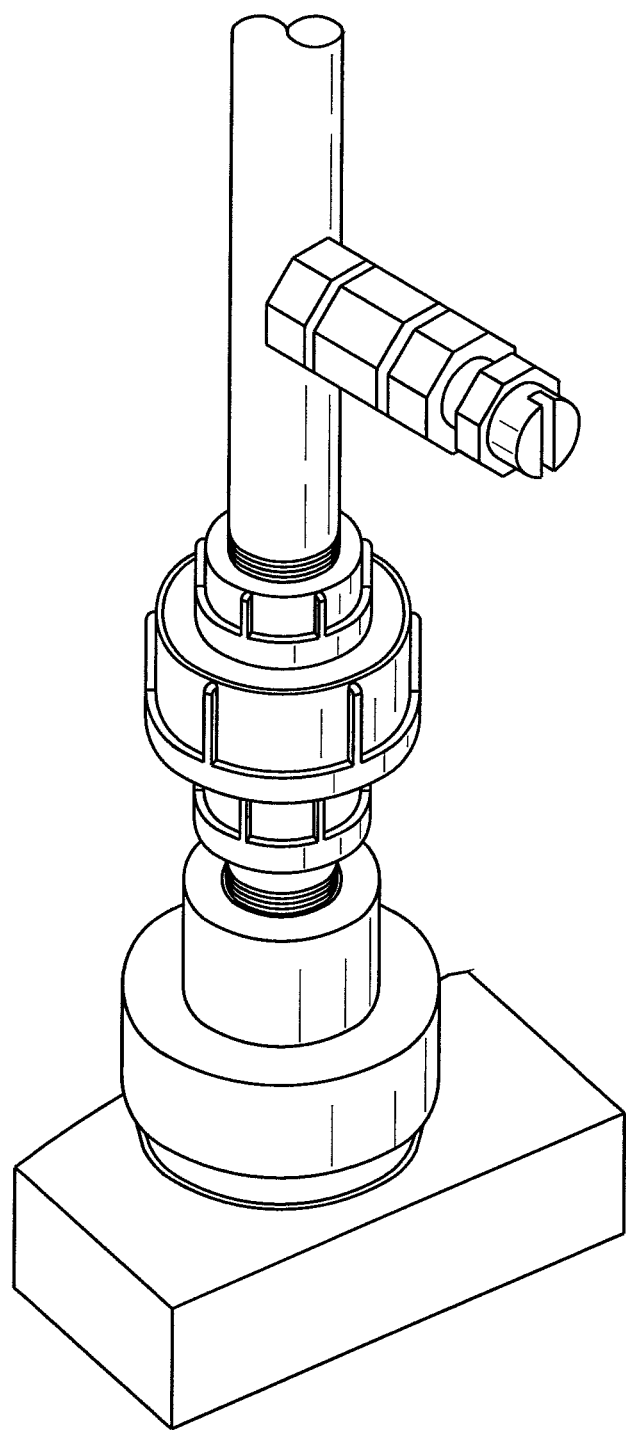
FIG. 6 is an enlarged view of an end of the spray bar remote from the drive assembly.

As particularly evident in FIG. 4, the motor 142 and drive linkage assembly 146 is located externally of the test cabinet. A mount 170 supports the variable speed motor 142 along an external wall of the housing. A spray bar/drive linkage 180 is disposed on an external surface the wall while a shaft seal 182 and shaft collar 184 are located within the test chamber and support the proximal end of the spray bar 130. An inlet 186 is provided through the hub 182 supply the solution to the hollow tube configuration of the spray bar. In this manner, the motor, drive links, etc. are all located externally of the tank and are thus not subjected to the corrosive effect within the test chamber. On the other hand, the spray bar 130, shaft collar 184, shaft seal 182, nozzles 160, etc. are all preferably formed from a non-corrosive material, e.g. plastic, that is able to withstand the corrosive effect of the harsh environment within the test chamber.

The disclosure has been described with reference to the preferred embodiments. Obviously, modifications and alterations will occur to others upon reading and understanding the preceding detailed description. It is intended that the disclosure be construed as including all such modifications and alterations.

I claim:

1. An automated oscillating solution spray manifold assembly for a corrosion testing chamber configured to introduce a fluid into a cavity of a test cabinet that is configured to receive associated workpieces through an opening; the manifold assembly comprising:
    a motor having an output shaft for driving a linkage assembly, wherein the motor and the linkage assembly are located outside of the cavity; and
    a spray bar connected to the linkage assembly having a plurality of openings spaced along a surface of the bar, wherein the linkage assembly is configured to rotate the spray bar in a desired oscillatory movement such that fluid can be dispensed through the openings and into the test cabinet.

2. The manifold assembly of claim 1, wherein the spray bar has an elongated conformation.

3. The manifold assembly of claim 1, wherein nozzles are mounted to the openings on the bar.

4. The manifold assembly of claim 3, wherein fluid is distributed from the nozzles such that a fan-like pattern sprays from one nozzle and substantially overlaps with spray from at least one adjacent nozzle.

5. The manifold assembly of claim 1, wherein the spray bar is located towards an upper portion of the cabinet.

6. The manifold assembly of claim 1, wherein the spray bar extends over substantially an entire length of the test cabinet cavity.

7. The manifold assembly of claim 1, wherein the spray bar includes a proximal end and an opposite distal end wherein the proximal end is attached to a wall of the cavity by a shaft collar and a shaft seal.

8. The manifold assembly of claim 7, wherein the shaft collar and shaft seal are located within the cavity of the test cabinet and the spray bar/drive linkage hub is located outside of the cavity.

9. The manifold assembly of claim 1, wherein the oscillatory movement of the spray bar extends through approximately a predetermined 90° angle.

10. The manifold assembly of claim 1, wherein the motor is secured to a motor mount on an exterior of the test cabinet.

11. The manifold assembly of claim 1, wherein the linkage assembly further comprises a first link, a second link and a third link wherein a first end of the first link is connected to the output shaft and a second end of the first link is connected to the second link, a first end of the third link is connected to a spray bar hub and a second end of the third link is connected to the second link.

12. A corrosion testing system comprising:
    a test cabinet having a hollow cavity dimensioned to receive associated workpieces through an opening; and
    a manifold assembly configured to introduce a fluid into the cavity of the test cabinet, the manifold assembly including:
        a motor having an output shaft for driving a linkage assembly from a location external to the test cabinet,
        a spray bar having a proximal end and an opposite distal end wherein the proximal end is rotatably attached to a wall of the test cabinet by a shaft collar and a shaft seal and has a plurality of openings spaced along a surface of the bar, and the spray bar being connected to the linkage assembly, wherein the linkage assembly is configured to rotate the spray bar in a desired oscillatory movement such that fluid can be dispensed through the openings and into the cabinet.

13. The corrosion testing system of claim 12, wherein the linkage assembly further comprises a first link, a second link and a third link wherein a first end of the first link is connected to the output shaft and a second end of the first link is connected to the second link, a first end of the third link is connected to a spray bar hub and a second end of the third link is connected to the second link.

14. The corrosion testing system of claim 13, wherein the output shaft imparts rotary motion onto the linkage assembly such that the spray bar results in oscillatory movement of about 90° within the cavity of the test cabinet.

15. The corrosion testing system of claim 12, wherein the test cabinet includes a lid that is configured to cover the opening and to allow selective access to the cavity in an open position and prevent access to the cavity in a closed position.

16. The corrosion testing system of claim 15, wherein the spray bar is mounted at an apex region of the lid on the test cabinet.

17. The corrosion testing system of claim 12, wherein the spray bar includes a hub that is configured to supply fluid from at least one of a first reservoir and a second reservoirs to the spray bar.

18. A method of testing corrosion of a workpiece comprising:
mounting at least one workpiece into a hollow cavity of a test cabinet;
introducing a fluid into the cavity of the test cabinet through a manifold assembly, the manifold assembly including a motor having an output shaft for driving a linkage assembly connected to a spray bar having a proximal end and an opposite distal end wherein the proximal end is rotably attached to a wall of the test cabinet by a shaft collar and a shaft seal and having a plurality of openings spaced along a surface of the bar;
locating the motor, output shaft, and at least a portion of the linkage assembly outside of the test cabinet cavity and thereby not subjected to a corrosive effect of the testing chamber;
rotating the linkage assembly to impart oscillatory movement to the spray bar; and
dispensing fluid through the openings such that the fluid is substantially distributed over the at least one workpiece for a predetermined period of time.

19. The method of testing corrosion of a workpiece of claim 18 further comprising the step of controlling a speed of the motor, a temperature level of the cavity, a humidity level of the cavity, and a salinity content of the fluid within the cavity of the test cabinet.

* * * * *